United States Patent
Adler, Jr. et al.

(10) Patent No.: US 12,427,338 B2
(45) Date of Patent: Sep. 30, 2025

(54) RADIOSURGICAL NEUROMODULATION CLOSE TO CRITICAL STRUCTURES

(71) Applicant: Zap Surgical Systems, Inc., San Carlos, CA (US)

(72) Inventors: John R. Adler, Jr., Stanford, CA (US); M. Bret Schneider, Menlo Park, CA (US)

(73) Assignee: Zap Surgical Systems, Inc., San Carlos, CA (US)

( * ) Notice: Subject to any disclaimer, the term of this patent is extended or adjusted under 35 U.S.C. 154(b) by 0 days.

(21) Appl. No.: 18/222,281

(22) Filed: Jul. 14, 2023

(65) Prior Publication Data

US 2024/0042237 A1    Feb. 8, 2024

Related U.S. Application Data

(62) Division of application No. 16/426,977, filed on May 30, 2019, now Pat. No. 11,745,029.

(60) Provisional application No. 62/678,098, filed on May 30, 2018.

(51) Int. Cl.
  *A61N 5/10* (2006.01)
  *A61K 51/04* (2006.01)
  *A61M 37/00* (2006.01)

(52) U.S. Cl.
  CPC ........ *A61N 5/1031* (2013.01); *A61K 51/0497* (2013.01); *A61M 37/0092* (2013.01); *A61N 2005/1098* (2013.01)

(58) Field of Classification Search
  CPC .......... A61N 5/1031; A61N 2005/1098; A61N 5/1084; A61K 51/0497; A61K 41/0038; A61M 37/0092

USPC ........................................................ 600/1–8
See application file for complete search history.

(56) References Cited

U.S. PATENT DOCUMENTS

| | | |
|---|---|---|
| 4,117,118 A | 9/1978 | Haerri et al. |
| 5,490,991 A | 2/1996 | Enriquez et al. |
| 5,614,547 A | 3/1997 | Hamilton et al. |
| 5,752,515 A | 5/1998 | Jolesz et al. |

(Continued)

FOREIGN PATENT DOCUMENTS

| | | |
|---|---|---|
| CN | 1767860 A | 5/2006 |
| CN | 107365799 A | 11/2017 |

(Continued)

OTHER PUBLICATIONS

"Chemical Components in the PDB", Protein Data Bank in Europe (PDBe), Available Online at: http://www.ebi.ac.uk/pdbe-srv/pdbechem/chemicalCompound/show/CPT, 1999, 1 page.

(Continued)

*Primary Examiner* — Sunita Reddy
(74) *Attorney, Agent, or Firm* — Kilpatrick Townsend & Stockton LLP

(57) ABSTRACT

Methods of treatment and treatment systems for performing radiomodulatory stereotactic radiosurgery to treat brain disorders in which target neural tissues associated with the brain disorder are sensitized to radiation by administration of a molecular substance and/or non-targeted critical structures are protected from radiation by a molecular substance, in order to treat disorders of brain circuitry. Specific embodiments disclose means for treating pain, obesity and drug addiction.

12 Claims, 11 Drawing Sheets

(56) References Cited

U.S. PATENT DOCUMENTS

| | | |
|---|---|---|
| 5,780,484 A | 7/1998 | Zelle et al. |
| 8,060,179 B1 | 11/2011 | Flynn |
| 8,337,382 B2 | 12/2012 | Schneider et al. |
| 8,709,380 B1 | 4/2014 | Weil et al. |
| 8,747,292 B2 | 6/2014 | Schneider et al. |
| 9,808,651 B2 | 11/2017 | Schneider et al. |
| 11,745,029 B2 | 9/2023 | Adler, Jr. et al. |
| 2003/0078499 A1 | 4/2003 | Eppstein |
| 2004/0147433 A1 | 7/2004 | Keep et al. |
| 2008/0003183 A1 | 1/2008 | Guo et al. |
| 2008/0192892 A1 | 8/2008 | Dilmanian et al. |
| 2008/0267865 A1 | 10/2008 | Sandberg et al. |
| 2009/0114849 A1 | 5/2009 | Schneider et al. |
| 2009/0298891 A1 | 12/2009 | Tofilon et al. |
| 2012/0093918 A1 | 4/2012 | Sanche et al. |
| 2012/0263675 A1 | 10/2012 | Wang et al. |
| 2013/0267757 A1 | 10/2013 | Schaffer et al. |
| 2013/0281890 A1 | 10/2013 | Mishelevich |
| 2016/0222100 A1 | 8/2016 | Monje-Deisseroth et al. |
| 2017/0043188 A1 | 2/2017 | Schneider et al. |
| 2017/0080088 A1 | 3/2017 | Savariar et al. |
| 2018/0098807 A1 | 4/2018 | Schwartz |
| 2018/0200385 A1 | 7/2018 | Malik et al. |
| 2018/0369409 A1 | 12/2018 | Liu et al. |
| 2019/0099491 A1 * | 4/2019 | Harvey ............... A61K 9/0053 |

FOREIGN PATENT DOCUMENTS

| | | |
|---|---|---|
| JP | 2008505144 A | 2/2008 |
| JP | 2015503585 A | 2/2015 |
| WO | 9622104 A1 | 7/1996 |
| WO | 0016794 A1 | 3/2000 |
| WO | 2016081835 A2 | 5/2016 |
| WO | 2016210376 A2 | 12/2016 |
| WO | 2018026738 A1 | 2/2018 |
| WO | 2019050551 A1 | 3/2019 |

OTHER PUBLICATIONS

Denekamp, "Relationship Between Radioprotective Agents and Tumor Therapy", Foreign Medicine (Clinical Radiology Section), Issue 1, Mar. 2, 1982.

Lamsam, et al., "A Review of Potential Applications of Mr-Guided Focused Ultrasound for Targeting Brain Tumor Therapy", Departments of Neurosurgery and Radiology, vol. 44, No. 2, Feb. 2018, pp. 1-7.

Levite, "Glutamate Receptor Antibodies in Neurological Diseases . . . and Can Be Removed or Silenced in Some Patients by Immunotherapy", J Neural Transm (Vienna), vol. 121, No. 8, Aug. 1, 2014, pp. 1029-1075.

Ling, "Research Progress of Radiation Protective Agents and Radiation Sensitizers", International Journal of Radiation Medicine and Nuclear Medicine, Issue 1, Feb. 28, 1992, 2 pages.

Luo, et al., "Dopaminergic Neurons and Brain Reward Pathways: From Neurogenesis to Circuit Assembly", The American Journal of Pathology, vol. 186, No. 3, Mar. 2016, pp. 478-488.

Pan, et al., "Nano-Chitosan Effect on Ion-Heavy Radiation Protection and Sensitization", Chinese Journal of Tissue Engineering Research, vol. 3, 2012, pp. 409-412.

Supprian, et al., "The Fornix of the Human Brain: Evidence of Left/Right Asymmetry on Axial MRI Scans", Surg Radiol Anat., vol. 19, No. 2, 1997, pp. 105-109.

Samiotaki et al., "Pharmacokinetic analysis and drug delivery efficiency of the focused ultrasound-induced blood-brain barrier opening in non-human primates", Magn Reson Imaging 37, pp. 273-281, Apr. 2017.

* cited by examiner

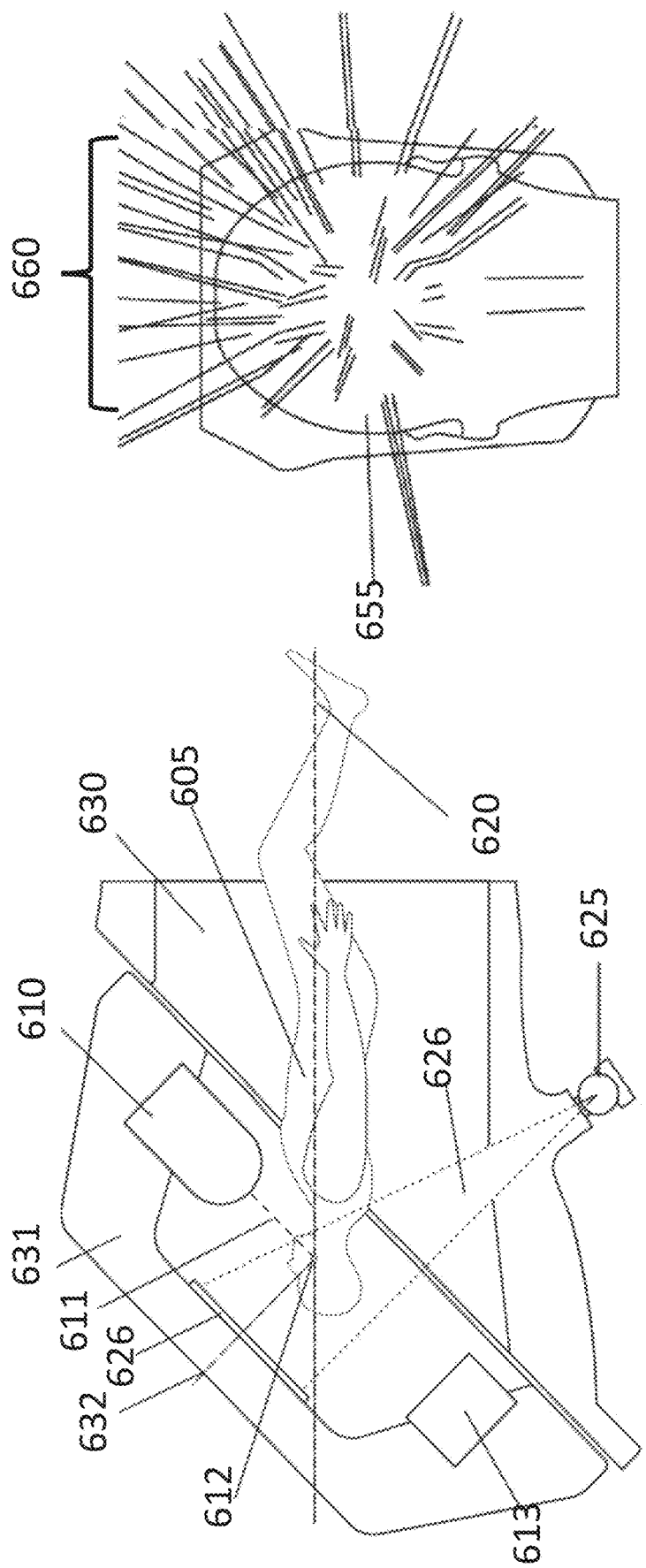

RADIOSURGICAL NEUROMODULATION CLOSE TO CRITICAL STRUCTURES

CROSS-REFERENCES TO RELATED APPLICATIONS

The present application is a divisional of U.S. Non-Provisional application Ser. No. 16/426,977 filed May 30, 2019, which claims the benefit under 35 USC § 119(e) of U.S. Provisional Appln. No. 62/678,098 filed May 30, 2018; the full disclosure of each which are incorporated herein by reference in their entirety for all purposes.

This application is generally related to the following U.S. patents and applications: U.S. Pat. No. 8,337,382 issued on Dec. 25, 2012; U.S. Pat. No. 8,747,292 issued on Jun. 10, 2014; U.S. Pat. No. 9,808,651 issued on Nov. 7, 2017; and PCT Application PCT/US2017/054880 filed Oct. 3, 2017; published as WO 2019/050551; each of which are incorporated herein by reference in their entirety for all purposes. This application is also generally related to the following publication: Samiotaki et al. "Pharmacokinetic analysis and drug delivery efficiency of the focused ultrasound-induced blood-brain barrier opening in non-human primates", *Magn Reson Imaging* 37, pp. 273-281, April 2017, the entire contents of which is incorporated herein by reference for all purposes.

BACKGROUND OF THE INVENTION

Radiomodulation (RM, radiosurgical neuromodulation) involves the use of radiosurgery to alter neuronal activity without killing cells or producing a lesion. Because the edge of even highly collimated beams of ionizing radiation is not a step function but rather a gradually diminishing curve of radiation, the gradient perpendicular to the direct path of the beam spreads into non-targeted tissue. Therefore, RM of precise areas of the brain, particularly those that are adjacent to critical anatomy of the brain, is technically difficult to achieve without this nearby anatomy being irradiated and injured. Radiation-induced alteration of brain areas close to the targeted areas is potentially dangerous, as it may result in side effects from the procedure, like neurological deficits, or may induce effects opposite to the intended goal of a specific radiomodulation procedure.

Radiosensitizers have been developed for wide-beam radiation therapy that permit lower radiation doses to kill a tumor. Radioprotectants have also been developed for systemic reduction of harm from ionizing radiation exposure. The application of molecular compounds like radiosensitizers and radioprotectants requires either acceptance of widespread non-targeted uptake, or invasive injection, for example during a surgical procedure. In general, it has not been possible to deposit either radiosensitizers or radioprotectants to specific locations inside the body without utilizing an invasive procedure.

By design, radiomodulation alters the function of all neurons within a precise volume of targeted brain, i.e. it has "anatomic specificity". Of note, the effect from ionizing radiation is not selective for any specific class of neurons within this brain volume, for example neurons which might be primarily responsible for a specific pathological brain circuit. Therefore, it would highly desirable to skew the effects of radiomodulation towards the pathologic neurons within the target region, thereby providing a form of "cell-type specificity".

BRIEF SUMMARY

To achieve the goal of providing radiomodulation with cell-type specificity, anatomically targeted radiomodulation can be combined with systemically administered molecules that have both a high affinity for certain neuronal types and which interact with and alter the effects of ionizing radiation in a manner that enables greater therapeutic selectivity. Such an approach provides safer treatment as well as greater therapeutic efficacy.

In one aspect, the present invention pertains to methods of treatment that include the selection of a targeted circuit node or tract connecting nodes ("target"), and identication of nearby critical structures of the brain, then delivering a radiosensitizing agent to a radiomodulation target, and/or radioprotectant agents to the nearby non-targeted critical structures prior to delivering a cellulary-non-lethal dose of ionizing radiation delivered by stereotactic radiosurgery. In some embodiments, the delivery of these agents may be accomplished by anatomically specific methods, for example, by use of ultrasound. In some such embodiments, methods utilize targeted focused ultrasound with systemically infused microbubbles to temporarily open the blood-brain barrier prior to delivering radiosensitizer and/or radioprotectants systemically and subsequent radiomodulation. Alternatively, the delivery of these agents may be accomplished by cell-type specific methods such use of a radiosensitizer or radioprotectant that is conjugated with a molecule with an affinity for unique molecular features of the target or critical structure, respectively, then delivered it systemically to the patient prior to radiomodulation. In this manner, the targeted area of the brain is modulated in activity level without injuring the cells in the target zone or nearby critical structures. The purpose of these steps is to treat a functional brain disorder, including psychiatric disorders such as behavioral disorders. Such methods are useful for treating a diverse range of disorders, including but not limited to, chronic intractable pain, eating-related disorders such as hyperphagia associated with obesity, and drug addiction.

In another aspect, the invention pertains to a treatment system that includes one or more radiosensitizer and/or radioprotectant substances having an affinity for certain types of brain cells; a blood-brain barrier permeator configured to permeate a blood-brain barrier of the brain to allow delivery of the one or more substances across the blood-brain barrier; and a radiation delivery system configured to deliver radiation to the target tissue at a therapeutic dose whereby treatment of targeted neural cells is enhanced and/or alteration of non-targeted tissues of critical structures of the brain is avoided by the presence of the one or more substances. In some embodiments, the radiation treatment system includes a processor configured to direct radiation from the radiation delivery system outside the patient, through a skull of the patient and into the brain of the patient along a plurality of beam paths directed from varying directions so as to intersect with targeted neural cells. In some embodiments, the permeator comprises an ultrasound delivery system and includes an imaging system for identifying a location to direct ultrasound from the ultrasound delivery system to temporarily permeate the blood-brain barrier for molecular compounds that would otherwise be too large to pass through to brain cells. In some embodiments, the imaging system is an Mill system and the ultrasound system comprises a high frequency ultrasound source.

BRIEF DESCRIPTION OF THE DRAWINGS

FIG. 4A illustrates an exemplary radiosurgical apparatus use for radiomodulation (RM), in accordance with some embodiments.

FIG. 4B illustrates the plethora of radiation beam trajectories used to carry out radiomodulation in an example system, in accordance with some embodiments.

DETAILED DESCRIPTION

Figure 1:
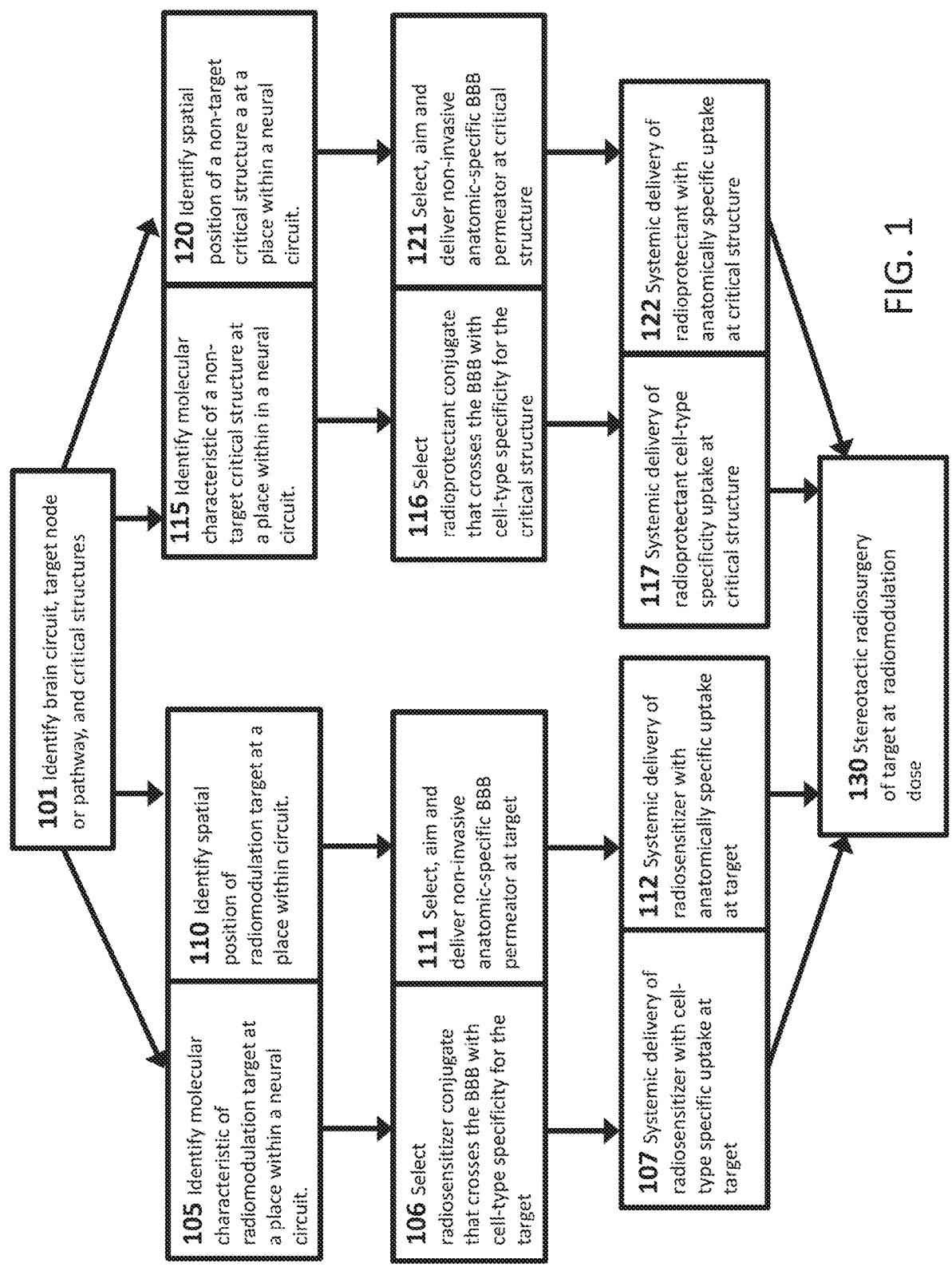
FIG. 1 illustrates an overview of the steps of an exemplary method, in accordance with some embodiments of the invention.

Radiomodulation (RM, radiosurgical neuromodulation) is the use of radiosurgery to alter neuronal activity functionally, without killing cells or producing a lesion. In the present invention, targeted areas of the brain, which can be either circuit nodes or pathways nodes, within a brain circuit, are modulated in activity level, while protecting nearby non-targeted critical structures from radiation effects. Critical structures may be near but separate from the target zone, or may be within the target zone but have distinguishing aspects.

In one aspect, radiosensitizers are deposited within brain areas that one wishes to modulate and radioprotectants are deposited in those brain areas in which one wants to prevent alteration. Depositing of radiosensitizer and/or radioprotectant substances can be performed in a number of ways, for example, by one or more of two methods: 1) temporarily opening the blood-brain-barrier (BBB) in a chosen anatomical spot, for example with MRI-guided focused ultrasound, generally in combination with systemically delivered microbubbles. 2) molecular targeting by utilizing a radiosensitizer or radioprotectant, respectively, conjugated to a molecule with specificity for the intended target, or non-target critical structure, and which can cross the BBB. As described herein, the term "conjugate" is used to mean to join two or more molecular structures regardless of the method of joining.

In one aspect, the methods described herein are used to treat functional disorders of the brain, including neurological and psychiatric disorders such as behavioral disorders. Such disorders can include but are not limited to: chronic pain, hyperphagia associated with obesity, and drug addiction.

In another aspect, the methods described herein are used to treat pathologies such as brain tumors that reside close to critical structures. In such disorders, an approach intended to be destructive to the targeted cells is desired. Such disorders may include, but are not limited to gliomas, oligodenrogliomas, menigiomas, chordomas, lymphomas, medulloblastomas, schwannomas, and metastatic brain tumors. It is appreciated that any of the concepts described herein can be utilized to facilitate destruction of target tissues by irradiation and inhibiting damage to nearby critical structures.

Radiosensitizers include, but are not limited to: fluoropyrimidines, gemcitabine platinum analogs such as cisplatin, misonidazole, metronidazole, hypoxic cytotoxins such as tirapazamine, oxygen, NBTXR3, nimoral, trans sodium crocetinate (TSC), NVX-108. Radioprotectants include, but are not limited to: hydroxytryptamine, cobalt chloride, deferoxamine, clioquinol, isofluran, oakadaic acid, vanadate, tilorone, baicalein, FG-4497, superoxide dismutase, glutathione, N-acetyl-cysteine, amifostine, fullerenois, cerium oxide, tempol, resveratrol, butin, vectors with repair enzymes, sodium orthovenate, antisense-PUMA, inhibitors of GSK-3β, HPV 16 E5 viral protein, angiotensin receptor blockers, flagellin analogues, RTA401, autophagy modulators, haemopoetin growth factors, keratinocyte growth factor, becaplermin, telbermin, FGF-P peptide, FG1:FGF2 chimeric GF, Velafermin, Tenovil, Delavo, SeV-mediated transfer of IL-10 gene, IL-10 inducers, Infliximab, Tolcizumab, IL-6 blockers, pravastatin, VEGF blockers, TNP-470, HIF blockers, TGFβ blockers, PDGFR inhibitors, HGF gene transfer, retinoic acid, anti-bFGF, ACE inhibitors, COX inhibitors, INGN201, MDM2 inhibitors, oblimersen, sodium, vanillin derivatives, Avotermin, NF-κB inducers, macrophage activation, suppressors, gap junction inhibitors, NOS inhibitors, macrophage activation inhibitors, and demethylation targeting agents.

Means for getting a drug selectively past the BBB may include temporarily rendering the BBB permeable by means such as mechanical disruption created with precisely guided (e.g. MRI-guided) targeted high intensity focused ultrasound (e.g. MRgFUS) or similar function device, typically in combination with systemically injected microbubbles, as described by Samiotaki and colleagues. This allows substances including larger molecules that would otherwise be prevented from reaching the brain to cross over from the system circulation to the brain parenchyma. Ultrasound can be focused more tightly than ionizing radiation, with a steeper falloff of intensity at the outer margins of the treated region. Thus a MRgFUS-permeated blood brain barrier permits radiosensitizers or radioprotectants to reach those areas of the brain that are specifically treated with the ultrasound. For this reason, MRgFUS in combination with systemically injected microbubbles is an improved way of preparing small areas (e.g. 5 mm wide or less, about 3 mm wide) of the brain for later radiomodulation. In this way, even molecules that are too large to pass an intact BBB (generally larger that 600 Daltons (Da), or with extreme lipophilicity or hydrophilicity) may be brought to targeted tissue or critical structures.

In other embodiments, the radiosensitizer and/or radioprotectant substances are carried by the microbubbles themselves. The microbubbles will be broken by the MRI-guided focused ultrasound at the area to be protected during opening the blood-brain-barrier. Then, the radiosensitizer and radioprotectant are released at a respective area. The size of microbubbles, in some embodiments, may be relatively small (e.g. smaller than a red blood cell). If larger microbubbles are selected, one advantage is the power or magnitude of ultrasonic can be lowered, but the disadvantage is that the microbubbles may collapse before reaching the target area. Thus, in some embodiments, it is desirable to utilize a microbubbles having a size from 2 µm to 6 µm.

In an alternative embodiment, a molecule may be brought across the BBB to the targeted cell type if the molecule has an affinity for the targeted cellular receptors within the target area of the brain being systemically injected, for example a radiosensitizer conjugated to cell-type antibody or neurotransmitter receptor antagonist. As described herein, the term "conjugate" is used simply in the sense of joining two or more molecules regardless of means. The conjugated molecule must have moderate lipophilicity to prevent excessive binding to plasma but still permit binding to neurons, and, the molecular mass of the conjugate must be less than 600 Da in order to permit blood-brain barrier passage. In one such example embodiment, a dopaminergic brain node is targeted with radiosensitizer metronidazole (171.6 Da) conjugated to a dopamine type 2 antagonist like raclopride (molecular mass of 347.236 Da), with the resultant conjugate molecule with a mass of 518.836 Da (plus the mass of any additional molecule required for the conjugation), and moderate lipophilicity. After the conjugate molecule docks in place at the dopamine receptor, it is taken up by the neuron by endocytosis, and transported throughout the cell by axonal transport. Alternatively, one can target dopaminergic cells within a target area while radioprotecting serotonergic, noradrenergic, cholinergic, GABAergic and glutaminergic neurons using radioprotectant conjugated with molecules of the requisite cell-type specificity, molecular mass and lipophilicity. Examples include tropiseteron (284.353 Da) for serotoninergic cells; propranolol (259.34 Da) for adrenergic cells; atropine (289.369 Da) for muscarinic cholinergic cells; flumazenil (303.288 Da) for GABAergic cells; and methoxetamine (247.33 Da) for NMDA/glutaminergic cells. As needed for BBB penetration without excessive binding in plasma, hydroxyl groups on the molecule may be chemically covered or exposed to decrease and to increase, respectively, lipophilicity.

For the radiomodulation procedure and any focused ultrasound procedure that precedes it, CT and MM are taken of the patients head and brain, and the fused images are used to guide the ultrasound and stereotactic radiosurgery procedure. Following delivery of radiosensitizers and/or radioprotectants to the target and critical structures, respectively, stereotactic radiosurgery is performed in a manner that produces radiomodulation as described in U.S. Pat. Nos. 8,337,382, 8,747,292, and 9,808,651, at a dose of approximately 20 to 60 Gy. At this radiomodulation dose, the targeted area of the brain is modulated without killing the cells in the target zone.

In one embodiment, the MRI and CT images may be used to create a 2D or 3D model of targeted areas and those requiring protection from radiation. Such a model is useful for guiding the opening of the blood-brain-barrier with focused ultrasound, and for delivering the radiomodulation dose of ionizing radiation. From such a model, a treatment plan for focused ultrasound, and a treatment plan for delivery of radiation may be determined.

In a preferred embodiment, chronic, intractable pain is treated by a combination of MRgFUS-facilitated permeation of the target and radiosensitization of the target (specifically the centromedian and parafascicular nuclei, or the lateral aspect of the medial dorsal nucleus of the thalamus), first permeating the blood brain barrier of the target regions with MRgFUS with microbubbles, then systemically administering radiosensitizer, and then conducting stereotactic radiosurgery-enabled radiomodulation. Use of ultrasound is most useful when a molecule is too large or too electrostatically or chemically too large to otherwise pass through the blood brain barrier, thus expanding the range of molecules that can be selected for this purpose. The deposition of a radiosensitizer within a targeted cell permits a lower dose of radiation to be used for radiomodulation than would be needed without a radiosensitizer. In this manner, radiomodulation of very small areas within the medial aspect of the thalamus is accomplished with minimal effects upon the surrounding nuclei that one does not wish to alter.

Optionally, a radioprotectant may be administered, either systemically following permeation of the BBB of the non-targeted critical structures, or by using a low molecular mass radioprotectant with moderate lipophilicity that can cross the BBB and bind to targeted areas. As one example, to protect a serotonergic critical structure, radioprotectant amifostine (214.224 Da) might be conjugated with a molecule with affinity for the critical structure's cell type that one wishes to protect, like serotonin antagonist ondansetron (combined mass 507.522 Da, with moderate lipophilicity). In this manner, a moderate dose of radiation (for example, 10 to 60 Gray) delivered to the area of the target will have a minimal effect upon surrounding critical structures. In this way, chronic, intractable pain may be mitigated with few if any side-effects.

In an alternative embodiment, the therapy may treat overeating behavior (hyperphagia) by targeting for downmodulation a very small portion of the hypothalamus known as the lateral hypothalamic area without affecting the medial hypothalamus (the latter producing an undesirable opposite effect of increased appetite when down-modulated). In this case, the targeted lateral hypothalamic area may be radiosensitized by first permeating the blood brain barrier with MRg-FUS, in combination with systemically injected microbubbles, aimed at that same area. Then a radiosensitizing agent may be injected systemically (or to a major brain perfusioning arterial pathway such as the carotid artery or subclavian artery). The radiosensitizing agent will be selectively taken up in the brain area in which the blood brain barrier has been permeated (in this case, the lateral hypothalamic area). Radiomodulation is then conducted. Optionally, a radioprotectant may be administered, for example, by using molecular targeting of a conjugate of an antibody to the cell type that one wishes to protect, and the radioprotectant molecule. In this manner, a moderate dose of radiation (for example 10-60 Gray) delivered to the general area of targeted and non-targeted regions will have an amplified effect upon the small targeted area, and a diminished effect upon surrounding non-targeted regions including critical structures. In this manner, the overeating behavior associated with obesity are mitigated.

In yet another alternative embodiment, the symptoms of drug addiction are targeted for radiomodulation in order to treat the symptoms. To accomplish this, one targets for radiosurgical down-modulation a very small portion of the brain known as the nucleus accumbens, in which there is an excess of dopaminergic activity. Complicating the procedure, however, are the presence of nearby non-targeted critical brain structures, neuronal tracts that transmit their signals with GABA. Because stereotactic radiosurgery delivers some radiation to non-targeted critical areas, this radiosurgery alone would pose risk of side effects. In this case, the targeted nucleus accumbens may be radiosensitized by systemically (or to a major brain perfusioning arterial pathway such as the carotid artery or subclavian artery), injecting radiosensitizer. An example radiosensitizer is metronidazole, conjugated to a dopamine receptor blocker raclopride while surrounding (creating a conjugate molecule with a mass of 445.396 Da plus that of additional elements needed to complete the conjugation, as is known in the art.) Alternatively or additionally, GABAergic tracts may be treated with radioprotectant such as amifostine conjugated with GABA antagonist flumazenil to make a conjugate with a mass of 517.444 Da and moderate lipophilicity. The conjugate will then be selectively taken up in the brain area in which the antibody binds (in this case, the dopaminergic pathways), and the radioprotectant agent will be taken up in areas where GABA and glutamate antibodies bind. In this manner, a moderate dose of radiation (for example 10-60 Gray) may be delivered to the general area of targeted nucleus accumbens and non-targeted regions surrounding regions, and the non-targeted areas receiving radiation will be substantially protected, while the unprotected target will be down-modulated by the radiation received. Alternatively, the symptoms of drug addiction may be mitigated by down-modulating just the dopaminergic cells within the nucleus accumbens, while protecting the glutaminergic and GABAergic aspects of the nucleus accumbens, even though they all reside in the target zone. This may be accomplished by use of conjugated radiosensitizers or radioprotectants in the manner previously described. In these ways, the symptoms associated with drug addiction are mitigated.

FIG. 1 illustrates an overview of the steps to the method described. Two approaches to administering radiosensitizer substances to a target before performing stereotactic radiosurgery are detailed in steps 105 through 107 and steps 110 through 112, respectively. Two approaches to administering radioprotectant substances to critical structures before performing stereotactic radiosurgery are detailed in steps 115 through 117 and steps 120 through 122, respectively. It is appreciated that a treatment can utilize a single approach or any combination of the approaches described herein.

In step 101, one identifies the pertinent brain circuit associated with the brain disorder, the target one wishes to alter or modulate with the treatment (typically a target node or neural pathway), and critical structures nearby that must not be injured or altered. As described herein, target can refer to a targeted tissue, and typically refers to a place within a neural circuit or pathway, such as a node. In step 105, one identifies a unique characteristic of a radiomodulation target thereby providing cell-type specificity. This could be, for example, identifying a molecular characteristic such as dopamine type 2 receptors. In step 106, a radiosensitizer agent with cell-type specificity is selected. This may be, for example, raclopride (with its dopamine type 2 affinity) conjugated with radiosensitizer metronidazole (combined molecular mass of 518 g/mol, moderately lipophilic). In step 107, a radiosensitizer is brought across the BBB by the cell-type specificity of the systemic infusion of a radiosensitizer conjugated to a selective binding molecule. In step 130, stereotactic radiosurgery with a radiomodulation dose and technique is carried out on the target.

In step 110, the spatial position of a radiomodulation target is identified thereby providing anatomic specificity. This is typically done with a combination of spatially precise CT data set spatially fused to one or more MRI data sets. The target and nearby critical structures (areas that one does not wish to affect with radiation) are demarcated. In step 111, a means for non-invasive BBB permeation is selected, aimed and delivered to target with spatial/anatomic specificity. Use of ultrasound is most useful when a molecule too large or too hydrophillic to otherwise pass through the blood brain barrier. An example is selecting, aiming and applying MRg-FUS stereotactically upon the target. In step 112, permeation of the BBB is achieved, for example by use of spatially located focused ultrasound such as MRg-FUS with subsequent systemic infusion of a radiosensitizer. Again, in step 130, stereotactic radiosurgery with radiomodulation dose and technique is carried out on the target.

In step 115, unique molecular characteristic of non-target critical structures are identified, thereby providing cell-type specificity. For example, as shown in FIG. 6B, while the targeted nucleus operates principally on dopamine, while nearby non-target critical structures and pathways are glutaminergic and GABAergic. In step 116, a radioprotectant with cell-type specificity is selected. In the case of GABA, for example, GABA antagonist flumazenil is conjugated with radioprotectant tempol (combined molecular mass <600 Da, moderate lipophilicity) by means known in the art. In step 117, a radioprotectant is brought across the BBB via cell-type specificity, including systemic infusion of a radioprotectant conjugated to a selective binding molecule such as an antibody to a unique molecular characteristic of the critical structure, and taken up into the axon and cell body by endocytosis and axonal transport. Again, in step 130, stereotactic radiosurgery with radiomodulation dose and technique is carried out on the target. At the same time, effect of radiation upon targeted dopaminergic neurons may be amplified by using dopamine antagonist raclopride conjugated to radiosensitizer metronidazole, which will dock the conjugated molecule will dock at D2 receptors and be taken into the cell by endocytosis.

In step 120, the spatial position of non-target critical structures are identified, thereby providing anatomical specificity. This could be, for example, the identification of the stereotactic coordinates of non-targeted nuclei or neuronal tracts by use of coordinate-registered MRI. In step 121, means for non-invasive BBB permeation are selected and aimed and deliver to the critical structure with spatial/anatomic specificity. An example is selecting, aiming and applying MRgFUS stereotactically upon the critical structure. In step 122, a radioprotectant is brought across the BBB via anatomical specificity including, for example permeation of the BBB by use of a spatially targeted method such as MRg-FUS and subsequent systemic infusion of a radioprotectant. Again, in step 130 stereotactic radiosurgery with radiomodulation dose and technique is carried out on the target.

Figure 2A:
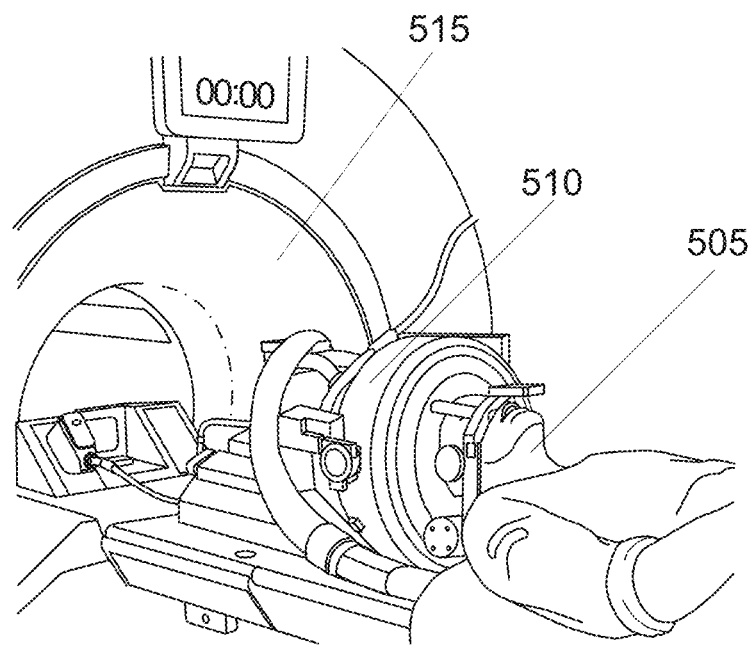
FIG. 2A illustrated an exemplary method by which the blood-brain-barrier may be temporarily opened by use of MRI-guided focused ultrasound, in accordance with some embodiments.

FIG. 2A shows patient 505 wearing a MRgFUS helmet 510, ready to be scanned in MRI scanner 515. MRgFUS helmet 510 contains ultrasound transducers that electronically focus on the brain target shown in the acquired MRI with submillimeter accuracy, and mechanically shake cell membranes in that target area, thus disrupting the BBB. Heating may also occur and contribute to the effect of increasing BBB permeability to molecules that are larger and more electrostatically incompatible with the pores of the blood brain barrier when in a normal state.

Figure 2B:
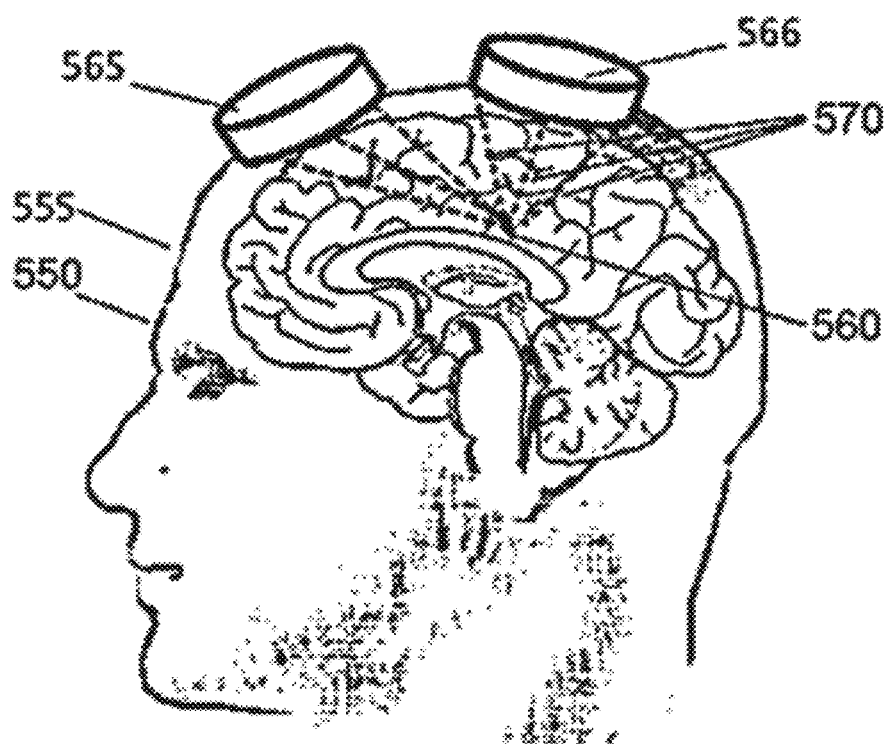
FIG. 2B illustrates ultrasonic transducers being electronically steered and focus on the intended target within the brain, in accordance with some embodiments.

FIG. 2B shows electronically directable and focusable ultrasound transducer 565 and 566 on the head of patient 550, with scalp 555. Ultrasonic energy 570 is combined land focused at ultrasound target 560 where it is used to temporarily disrupt the blood brain barrier, allowing passage of molecules that would otherwise be too large, electrostatically or chemically incompatible with the pores of the blood brain barrier in their normal state.

Figure 3:
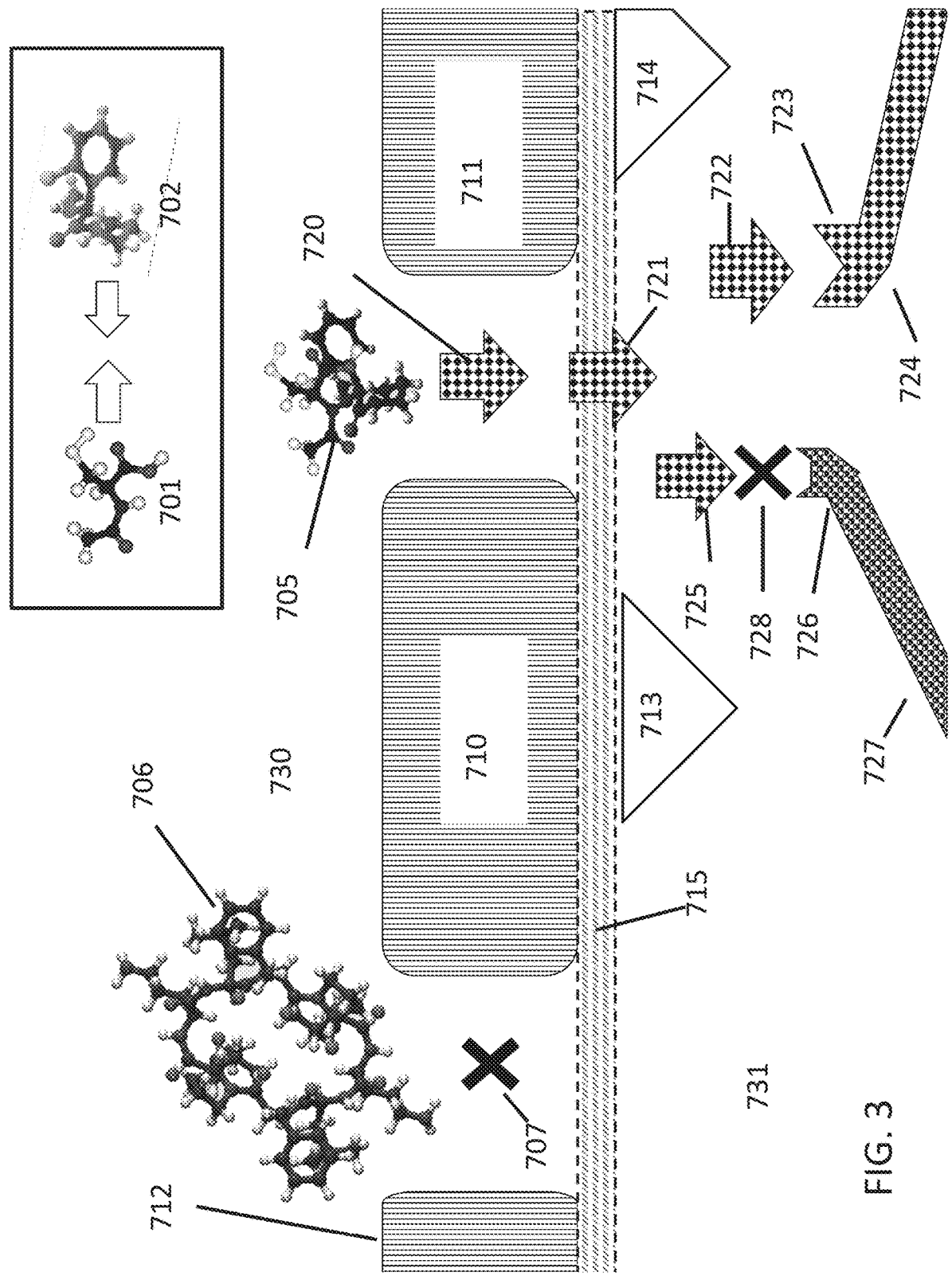
FIG. 3 illustrates novel molecular structures produced by conjugating a molecule with an affinity for a specific cell type with a molecule have radioprotectant properties, and how such molecules selectively radioprotect only cells of a predesignated type, in accordance with some embodiments.

FIG. 3 illustrates novel molecular structures produced by conjugating a molecule with an affinity for a specific cell type with a molecule have radioprotectant properties, and how that molecule selectively radioprotects only a predesignated cell type. FIG. 3 shows how conjugated N-acetylcysteine/ketamine molecule 705 passes 720 across the blood brain barrier from capillary lumen 730, between endothelial cells 710, 711 and 712, and across basement membrane 715 into brain parenchyma 731 which is adjacent to endothelial cells 710, 712 and 713 and basement membrane 715, and includes astrocyte foot processes 713 and 314.

First, radioprotectant N-acetylcysteine molecule 701 is conjugated to NMDA antagonist ketamine molecule 702 by organic chemistry methods known in the art to produce conjugated N-acetylcysteine/ketamine molecule 705. Conjugated N-acetylcysteine/ketamine molecule 705 passes 720 through gaps between endothelial cells 710, 711, and 712 and passes 721 through basement membrane 715. Meanwhile, peptide 706 is too large (molecular weight greater than 600 Daltons), and therefore unable to pass 707 through gaps between endothelial cells 210, 211, and 212.

Conjugated N-acetylcysteine/ketamine molecule fits 722 NMDA receptor 723 of glutaminergic neuron 724, where it is taken into glutaminergic neuron 724 by endocytosis. Meanwhile, when conjugated N-acetylcysteine/ketamine molecule 705 encounters 725 receptor 726, conjugate N-acetylcysteine/ketamine molecule 705 does not fit 728 into receptor 726 of non-NMDA neuron 727 (for example a GABAergic neuron. In this manner, only NMDA-glutaminergic neurons are imparted with the radioprotectant properties.

FIG. 4A illustrates a stereotactic radiosurgical system, used for radiomodulation. In this system by Zap Surgical Systems, Inc. (San Carlos, CA), patient 605 is treated with radiation beam 611 coming from linac 610 to target 612 with radiation that has passed through the patient and is finally absorbed at beam stop 613. Imaging radiation source 625 passes low levels of x-ray radiation through the head of patient 605, and creates a digital image on detector array 626. The radiosurgical system shown is self-shielded for radiation, and includes axial shield 630 which rotates about axis 620, and oblique shield 630. It is appreciated that various other treatment systems could be used, including a treatment system utilizing a single treatment beam as well as treatment systems having multiple beams directed to the target from multiple directions.

FIG. 4B shows the stereotactic radiosurgery system used for radiomodulation as shown in FIG. 3A sequentially or in parallel, which delivers multiple beams 660 of radiation through the patient 655. With all beams intersecting within the targeted tissue, the radiation dose at the target sums up while the peripheral areas of the patient receive relatively little radiation.

Figure 5A:
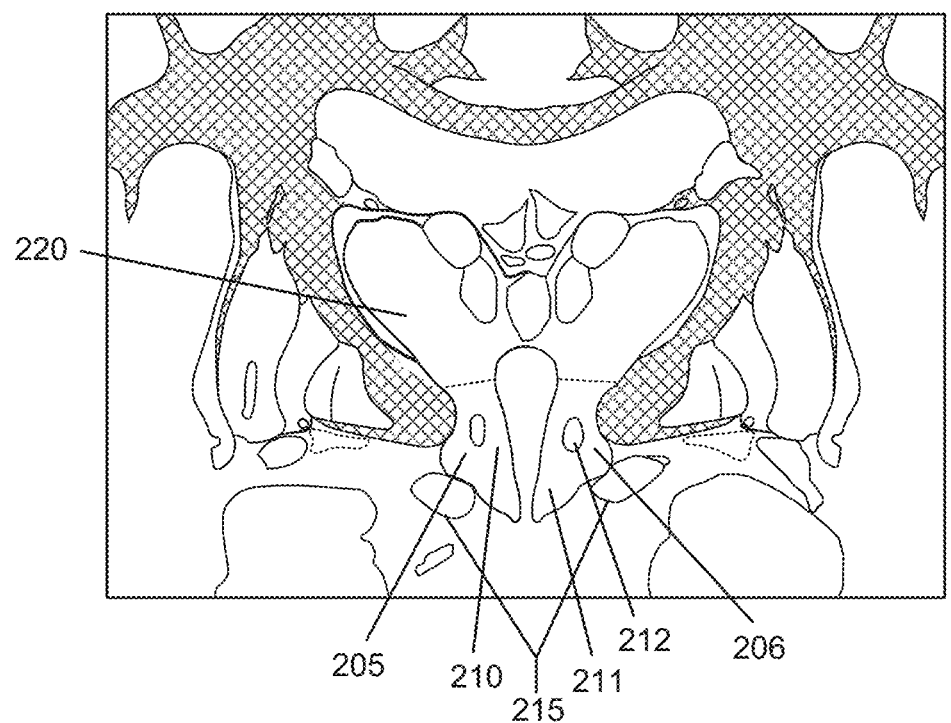
FIG. 5A illustrates a coronal view of the anatomy of the hypothalamus and numerous nearby anatomical structures within the brain.

FIG. 5A illustrates the anatomy of the hypothalamus and surrounding brain areas in coronal section at approximately 2× magnification. One will appreciate that there are numerous separate structures residing in a small space. Lateral hypothalamic areas 205 and 206, respectively are immediately next to the medial hypothalamus 210 and 211 respectively. Passing through the middle of the hypothalamus is the fornix column 212. Immediately beneath the hypothalamus are optic tracts 215, a critical structure to which damage must be avoided in order to prevent blindness. Above the hypothalamus is the ventrolateral nucleus of the thalamus 220. In treating this region, it is desirable to radiomodulate the lateral hypothalamic areas 205 and 206 while avoiding damage to the optic tracts, for example, by applying MRg-FUS to the lateral hypothalamic areas 205 and 206 and infusing radiosensitizer tirapazamine. Optionally, tirapazamine may be chemically joined to a molecule with specificity for the specific type of neuron being targeted so as to ensure greater specificity or where the radiosensitizer is deposited.

Figure 5B:
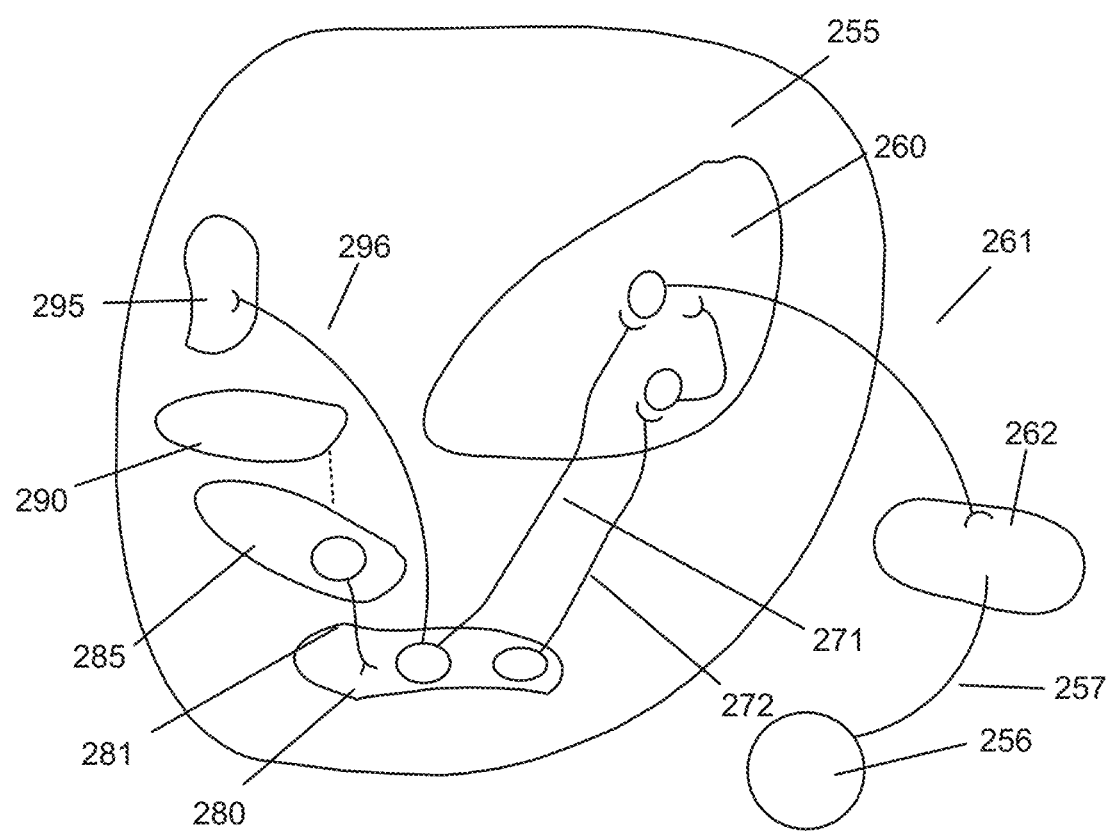
FIG. 5B illustrates the "appetite circuit" of the brain, to which the lateral hypothalamic area (LHA) is key.

FIG. 5B shows the neural circuit, the "hypothalamic appetite circuit" within which the aforementioned anatomy carries out its function. The circuit is composed of areas called nodes, and the white matter connections or tracts that lie between the nodes and transmit information between them. Hypothalamus 255 includes numerous nuclei including the lateral hypothalamic area (LHA) 260 which is connected by LHA-hindbrain tract 261 to hindbrain 262. Via a two-way connection 257, the hindbrain detects and responds to food intake 256 levels. Lateral hypothalamic area 260 is connected to the arcute nucleus of the medial hypothalamus by at least two pathways: neuropeptides: co-expressed NPY/Agrp 271 and co-expressed POMC/Cart 272. NPY and the melanocortin precursor, proopiomelanocortin (POMC) are expressed in adjacent, but distinct, subpopulations of arcuate nucleus neurons. Hypothalamic NPY/Agrp neurons 271, like PMC/Cart neurons 272 constitute a unique, separate cell types that are activated by fasting to stimulate food intake via a simultaneous increase of NPY and decrease of melanocortin. POM/Cart 272 provides input to lateral hypothalamic area 260 in a negative feedback loop with LHA-hindbrain neuron 261. Arcuate nucleus 280 receives input from ventral medial hypothalamus via neurons 281, and delivers messages to PVH 295 via neurons 296.

Figure 6A:
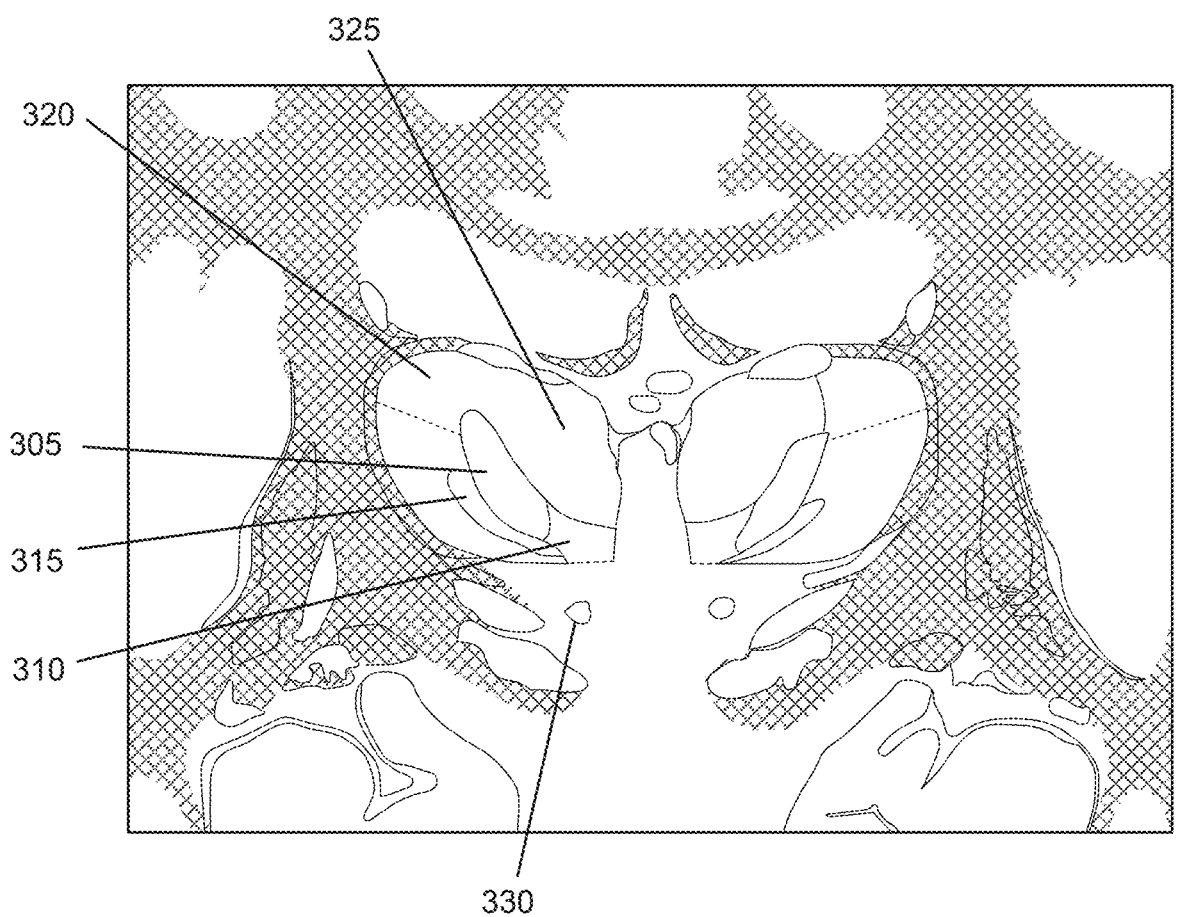
FIG. 6A illustrates a coronal view of the anatomy of the thalamus and numerous nearby structures within the brain.
Figure 6B:
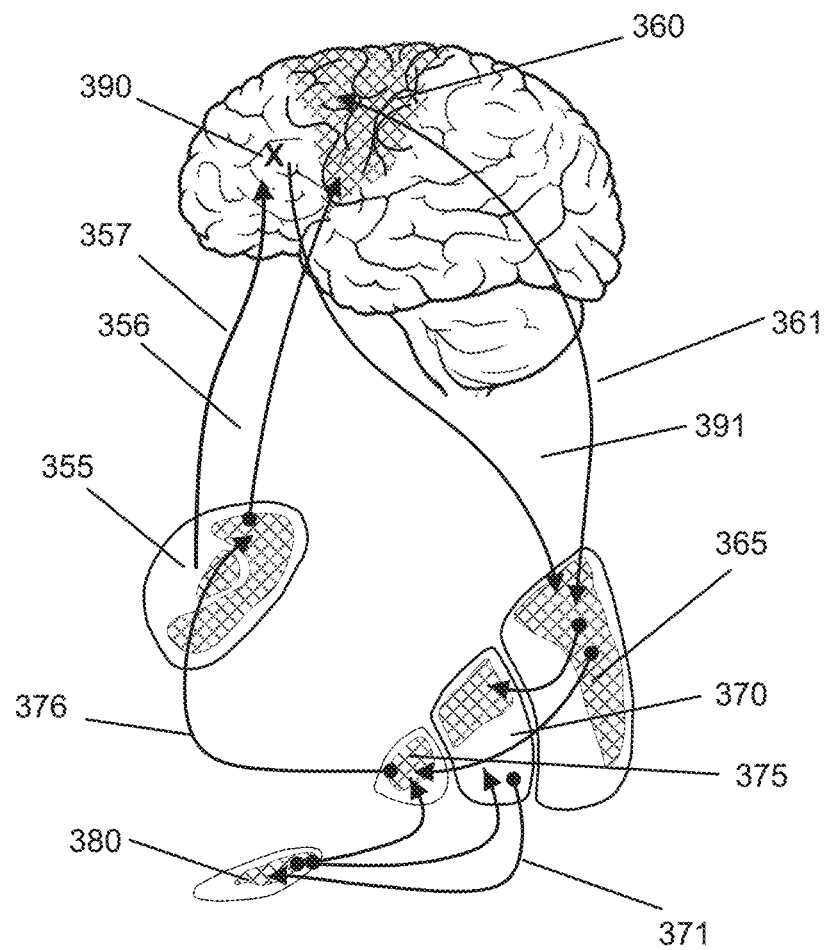
FIG. 6B illustrates a cortico-thalamic-cortical brain circuit that governs the perception of pain, and to which the thalamus is key.

FIG. 6A illustrates the anatomy of the thalamus and surrounding brain areas in coronal section at approximately 2× magnification. One will appreciate that there are numerous separate structures residing in a small space. Areas key to pain control are the centromedian nucleus 305 and the parafascicular nucleus 310. Beneath the thalamus is the optic tract 330, a critical structure to which damage must be avoided in order to prevent blindness. Adjacent to centromedian nucleus 305 are the critical structures of ventral posteromedial nucleus 315, and stria terminalis 320, both of which should avoid being modulated or damaged.

FIG. 6B shows the "thalamic pain circuit" in which the aforementioned anatomical regions carry out their function. The entire circuit consists of a several component neural circuits, of which the above anatomy is a portion. The circuit is composed of areas called nodes, and the white matter tracts form connections between the nodes. Thalamus 255 includes the centromedian nucleus and parafascicular nucleus as described in FIG. 5A. Pathways 356 and 357, extending to the sensory-motor cortex 360 and the dorsal anterior cingulate cortex 390, connect these regions respectively. Feedback from the sensory-motor cortex 360 is relayed to putamen 365 via tract 361. The signal in putamen 365 is then relayed to globus pallidus externa 370 and to globus pallidus interna 375 via connection 370. Signals for globus pallidus externa 370 and globus pallidus interna 375 are relayed to subthalamic nucleus 380, which also proves a feedback loop to globus pallidus externa 371. Signals from globus pallidus interna 375 are relayed in a feedback loop back to medial nuclei of thalamus 355. This series of circuit connections including feedback loops that serves to detect and regulate the perception of pain the body. In the context of the present invention, one could treat the centromedian nucleus 305 and parafascicular nucleus 310 without injuring the lateral areas of the thalamus by applying MRg-FUS in order to permit compounds to more specifically target the centromedian nucleus and parafascicular nucleus, then infusing radiosensitizer gemcitabine prior to proceeding with irradiation at a lower dosage (for example 10 Gy) than would be required without gemcitabine. Optionally, the radiosensitizer may be chemically joined to the radiosensitizer in order to provide more specificity as to where it is deposited. The use of the ultrasound permits molecules that would otherwise be too large, electrostatically or chemically incompatible for blood brain barrier pores in their natural state, thus expanding the range of molecular options.

Figure 7A:
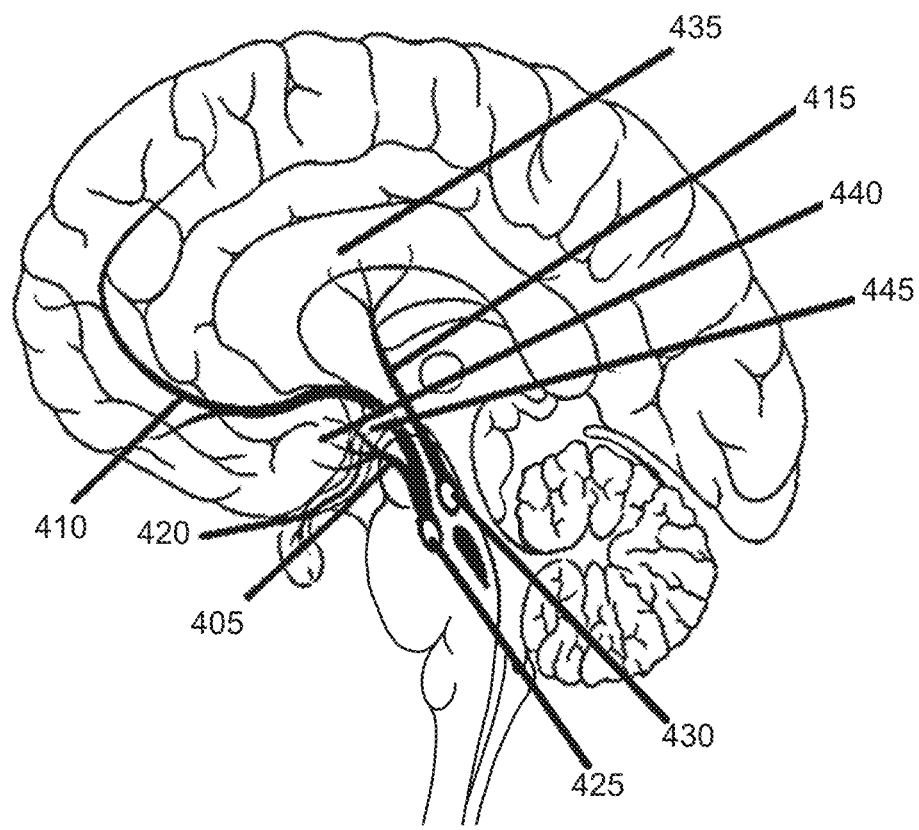
FIG. 7A illustrates the major dopamine pathways emanating from the ventral tegmental area (VTA), including the nucleus accumbens that is important for reward, such as that received from opiate, cocaine, alcohol tobacco and other drugs of abuse.

FIG. 7A describes the frontal lobe ventral tegmental circuit in which the nucleus accumbens and other pathways associated with the ventral tegmental area (VTA) stay in balance by feedback loops. As described in the description of 6B, different tracts operate with different neurotransmitters that are thus targetable on a molecular basis. Here in FIG. 7A, VTA 425 gives rise to the mesolimbic pathway 405 (which is important for mood, and the maintenance of addictive behavior in, for example, drug addiction), tuberoinfundibular pathway 420, mesocortical pathway 410. Substantial nigra 430 gives rise to nigrostriatal pathway 415, all of which are dopaminergic. Also shown are dorsal striatum 435, and nucleus accumbens 440, both dopaminergic. It will be appreciated that the nucleus accumbens is physically close to other brain areas and pathways. Accordingly, it would be difficult to radiomodulate, for example, the nucleus accumbens, without also affecting surrounding brain including the ventral pallidum. It would be yet more difficult to radiomodulate the dopaminergic portions of nucleus accumbens 440 without affecting the glutaminergic and GABAergic portions.

Figure 7B:
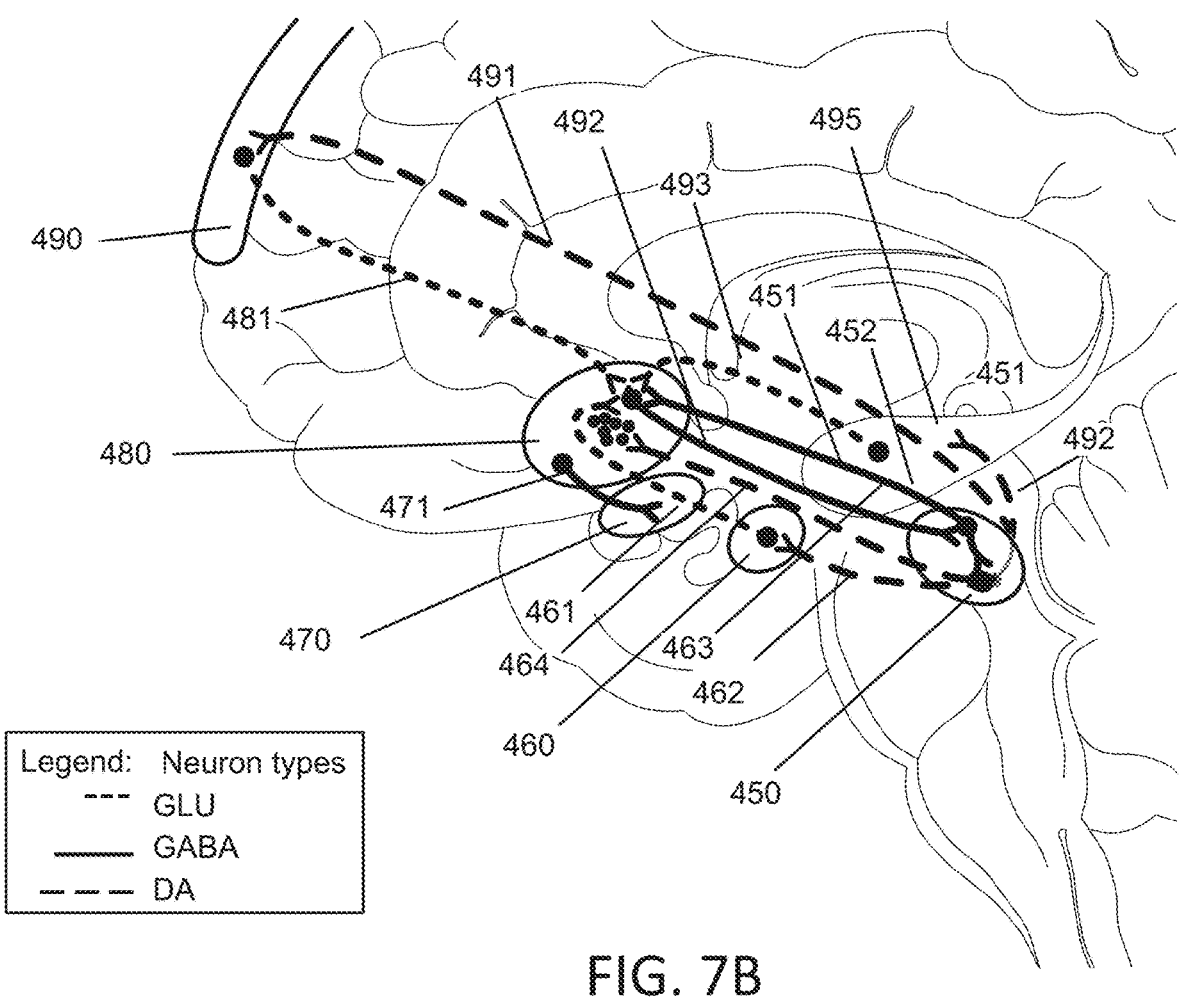
FIG. 7B describes the frontal lobe ventral tegmental circuit in which the nucleus accumbens and other structures associated with the ventral tegmental area (VTA) stay in balance by feedback loops, different tracts operating with different neurotransmitters that are thus targetable on a molecular basis and different types of neurons comprise the nucleus accumbens.

FIG. 7B describes the frontal lobe ventral tegmental circuit in which the nucleus accumbens and other structures and pathways associated with the ventral tegmental area (VTA) (in which the aforementioned anatomical regions are carry out their functions) stay in balance by feedback loops. The circuit is composed of areas called nodes, and the white matter tracts that connect the nodes. This system regulates not only the perception of reward, including the reward associated with use of drugs including opiates, cocaine, alcohol and tobacco. Different tracts operate with different neurotransmitters that are targetable on a molecular basis. Ventral temental area (VTA) 450 delivers excitatory dopamine to amygdala 460 via VTA-amygdala connection 462, to nucleus accumbens by VTA-amygdala tract 463, and also indirectly sents excitatory glutamate to nucleus accumbens 480, via amygdala-accumbens connection 461. From nucleus accumbens 480, at least four connections send signal back to VTA 450: excitatory dopaminergic accumbens-VTA connection 464, inhibitory GABAergic accumbens-VTA tract 492, and the inhibitory GABAergic bidirectional accumbens-VTA-accumbens tract 454, and inhibitory GABAergic accumbens-VTA tract 452. Additionally GABAergic accumbens-VTA tract 492 sends feedback inhibition back to the VTA 450 when receiving inhibitory signals from GABAergic VTA-accumbens tract 451, GABAergic hippocampus-amygdala tract 392, and GABAergic prefrontal-accumbens tract 491 VTA 450 also delivers dopaminergic signal along VTA-hippocampus tract 392, and dopaminergic signal along VTA-prefrontal tract 491. Amygdala 460 also received excitatory glutaminergic input from prefrontal-amygdala tract 481, and receives excitatory glutaminergic signal from hippocampus 495 along hippocampus-amygdala tract 493. Nucleus accumbens 480 also send and inhibitory glutaminergic signal along accumbens-ventral pallidum tract 471 to ventral pallidum 470.

It should be noted that nucleus accumbens 480 includes dopaminergic, glutaminergic and GABAergic neurons, with GABAergic accumbens-ventral pallidum tract 471, glutaminergic amydala-accumbens tract 461, dopaminergic VTA-accumbens tract 464 GABAergic accumbens-VTA tract 492, and VTA accumbens tract 451, glutaminergic hippocamal accumbens tract 493, and prefrontal-accumbens tract 481 all either originating or terminating in nucleus accumbens 480. In the context of the present invention, one can selectively modulate only the dopaminergic portions of nucleus accumbens 480, while leaving glutaminergic and GABAergic portions intact. This may be accomplished, for example, by radiosensitizing dopaminergic neurons with D2 antagonist raclopride (347 Da) conjugated with radiosensitizer metronidazole (171.16 Da), radioprotecting non-dopaminergic portions of nucleus accumbens 480 with GABA antagonist flumazenil (303.288 Da) conjugated with radioprotectant N-acetyl-cysteine (163.195 Da), and glutaminergic/NMDA antagonist ketamine (237.725 Da) conjugated with radiosensitizer vandate (183.907 Da) with glutaminergic NMDA antagonist ketamine conjugated with radiosensitizer misonidazole. Because the raclopride/metronidazole conjugate will only be taken up by dopaminergic cells, only dopaminergic cells will be radiosensitized. Furthermore, because the ketamine/n-acetyle-cyteine conjugate will dock only with NMDA receptors and be taken up into the glutaminergic neuron by endocytosis, only the NMDA neurons will be radioprotected.

While certain disorders of the brain and associated neural circuits and nodes have been detailed above, it is appreciated that the concepts described herein are applicable to treatment of various other disorders and targeted tissue, and various other neural circuits and portions of neural circuits and nodes. Further, while select radiosensitizer and radioprotectant substances have been described above, it is appreciated that various other substances can be utilized in accordance with the concepts described herein.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

In the foregoing specification, the invention is described with reference to specific embodiments thereof, but those skilled in the art will recognize that the invention is not limited thereto. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of treating a disorder of a brain of a patient, the method comprising:
   identifying a non-targeted critical structure physically close to a target tissue of a neural circuit of the brain;
   identifying a spatial position of the critical structure within said neural circuit;
   selecting, aiming and delivering a non-invasive anatomic-specific blood-brain barrier permeator to a blood brain barrier of the brain;
   delivering one or more molecular substances with anatomically specific uptake at the critical structure across the permeated blood-brain barrier, wherein the one or more molecular substances inhibit irradiation of the critical structure; and
   transmitting a cellularly sub-lethal quantity of ionizing radiation from outside the patient to the neural circuit, in a manner that the ionizing radiation delivers a therapeutic dose of radiation to the neural circuit while inhibiting damage to the critical structure,
   wherein the one or more molecular substances further comprise a substance with anatomic specific uptake at the target tissue of the neural circuit,
   wherein the substance has an affinity for a specific brain cell type.

2. The method of claim 1, wherein the transmitting the ionizing radiation comprises transmitting the ionizing radiation from a radiation source machine positioned outside the patient, through a skull of the patient and into the brain of the patient along a plurality of beam paths directed from varying directions in a manner as to intersect with the critical structure.

3. The method of claim 1, wherein the one or more molecular substances have an affinity for the specific brain cell type.

4. The method of claim 1, wherein the substance further comprising a radiosensitizer to facilitate radiation at the target tissue of the neural circuit.

5. The method of claim 1, wherein said permeator is focused ultrasound.

6. The method of claim 1, wherein the neural circuit comprises dopamine production neurons in a nucleus accumbens, and wherein transmitting the ionizing radiation comprises transmitting the ionizing radiation into a striatum of the patient which alter an amount of dopamine activity in the nucleus accumbens in a manner that symptoms of drug addiction are mitigated.

7. The method of claim 1, wherein the delivering one or more molecular substances comprises delivering a radioprotectant to non-dopaminergic neurons within a nucleus accumbens.

8. The method of claim 1, wherein the one or more molecular substances have cell-type specificity with an affinity for certain types of brain cells.

9. The method of claim 8, wherein the certain types of brain cells comprise brain neurons and the one or more molecular substances has a specific affinity for any of the following types of brain neurons: Glutamate (GLU) neurons; Gamma-aminobutyric acid (GABA) neurons; and Dopaminergic (DA) neurons.

10. The method of claim 1, wherein the critical structure is a hippocampus.

11. The method of claim 1, wherein the critical structure is an amygdala.

12. The method of claim 1, wherein the critical structure is an optic tract.

* * * * *